United States Patent
Gao (10) Patent No.: US 11,541,091 B2
(45) Date of Patent: Jan. 3, 2023

(54) PANAX PLANT EXTRACT AND PHARMACEUTICAL COMPOSITION AND USE THEREOF

(71) Applicant: Shanghai Huiyu Biomedical Technology Co., Ltd., Shanghai (CN)

(72) Inventor: Shangxian Gao, Shanghai (CN)

(73) Assignee: SHANGHAI HUIYU BIOMEDICAL TECHNOLOGY CO., LTD., Shanghai (CN)

( * ) Notice: Subject to any disclaimer, the term of this patent is extended or adjusted under 35 U.S.C. 154(b) by 110 days.

(21) Appl. No.: 16/479,221

(22) PCT Filed: Dec. 4, 2017

(86) PCT No.: PCT/CN2017/114497
§ 371 (c)(1),
(2) Date: Aug. 20, 2019

(87) PCT Pub. No.: WO2018/133563
PCT Pub. Date: Jul. 26, 2018

(65) Prior Publication Data
US 2021/0177923 A1    Jun. 17, 2021

(30) Foreign Application Priority Data

Jan. 22, 2017 (CN) .......................... 201710054498.3

(51) Int. Cl.
| | |
|---|---|
| A61K 36/258 | (2006.01) |
| A61P 25/28 | (2006.01) |
| A61P 3/06 | (2006.01) |
| A61P 3/10 | (2006.01) |
| A61P 15/00 | (2006.01) |
| A61P 35/00 | (2006.01) |
| A61K 9/20 | (2006.01) |
| A61K 31/7028 | (2006.01) |

(52) U.S. Cl.
CPC .......... *A61K 36/258* (2013.01); *A61K 9/2072* (2013.01); *A61K 31/7028* (2013.01); *A61P 3/06* (2018.01); *A61P 3/10* (2018.01); *A61P 15/00* (2018.01); *A61P 25/28* (2018.01); *A61P 35/00* (2018.01)

(58) Field of Classification Search
None
See application file for complete search history.

(56) References Cited

FOREIGN PATENT DOCUMENTS

| | | | |
|---|---|---|---|
| CN | 103463154 A | 12/2013 | |
| CN | 103610718 A | 3/2014 | |
| CN | 104487079 A * | 4/2015 | ............. A61P 35/00 |
| CN | 104487079 A | 4/2015 | |
| CN | 105273032 A | 1/2016 | |
| CN | 105968160 A | 9/2016 | |
| WO | WO-2007006208 A1 * | 1/2007 | ............... A61P 9/06 |

OTHER PUBLICATIONS

CN-104487079-A description translation Apr. 2015 (Year: 2015).*
CN-104487079-A claims translated Apr. 2015 (Year: 2015).*
CN-104487079-A translated description (Year: 2015).*
CN-104487079-A translated claims (Year: 2015).*
WO-2007006208-A1 translated doc (Year: 2007).*

* cited by examiner

Primary Examiner — Susan Hoffman
Assistant Examiner — Jacob A Boeckelman
(74) Attorney, Agent, or Firm — Bayramoglu Law Offices LLC (57) ABSTRACT

A *Panax* plant extract and a pharmaceutical composition and the use thereof. The mass ratio of Rk1 and Rg5 in the *Panax* plant extract is 1:1.0-1.5, and the content of Rg3, Rg5 and Rk1 in the extract is relatively high. The extract can be used to prepare a drug for treating chronic heart failure, coronary stable angina, arrhythmia, diabetes and complications thereof, Meniere's disease, hyperlipemia, fatty liver, Alzheimer's disease, dymenorrhea, metabolic syndrome, gout, tumours or vascular leak syndrome.

9 Claims, 1 Drawing Sheet

PANAX PLANT EXTRACT AND PHARMACEUTICAL COMPOSITION AND USE THEREOF

CROSS REFERENCE TO THE RELATED APPLICATIONS

This application is the national phase entry of International Application No. PCT/CN2017/114497, filed on Dec. 4, 2017, which is based upon and claims priority to Chinese Patent Application No. 201710054498.3, filed on Jan. 22, 2017, the entire contents of which are incorporated herein by reference.

TECHNICAL FIELD

This application involves a Chinese herbal extract and the preparation method thereof, specifically, a *Panax* plant extract and a pharmaceutical composition and the use thereof.

BACKGROUND

Known as the "king of all kinds of herbs" and "panacea", ginseng is the root of panax ginseng, an Araliaceae plant, and a rare medicinal herb renowned at home and abroad and used in China and East Asia for thousands of years. Studies found that ginseng contains ginsenosides, peptides and amino acids, vitamins, etc. Playing a major role in the efficacy of ginseng, ginsenoside widely acts on cardiovascular, nervous, immune and other human body systems, and shows unique effects in the treatment of CVD, metabolic disease, tumour, etc. About 40 ginsenosides, such as Rb1, Rb2, Rb3, Rc, Rd, Rg1, Rg2, Rg3, Rh1, Rh2 and Re, have been defined.

A lot of researches in recent years found that ginsenosides can exert their therapeutic action after being metabolized on specific physicochemical conditions or by bio-enzymes into secondary saponins that contain less sugar and can be directly absorbed by human body, such as Rg3, Rg5, Rh1, Rk1, Rh2, Rg2, C-K. Thus Rg3, Rg5, Rk1, Rh2, Rg2, C-K, etc are major active ingredients for ginseng's medical and healthcare functions.

GinsenosideRg3, GinsenosideRg5 and/or GinsenosideRk1 are partially hydrolyzed ginsenosides and secondary saponins removed from some of glycosylated degradation products with very strong biological pharmacological activity.

NOW, THEREFORE, this application is hereby made.

SUMMARY

The first invention of this application aims to provide a *Panax* plant extract.

The second invention of this application aims to provide the said pharmaceutical composition containing the *Panax* plant extract.

The third invention of this application aims to provide the said use of the *Panax* plant extract.

To accomplish the aims of the inventions of this application, this application adopts the following technical solution:

This application involves a *Panax* plant extract containing GinsenosideRg3, GinsenosideRk1 and GinsenosideRg5, the mass ratio of the said GinsenosideRk1 and GinsenosideRg5 is 1:1.0-1.5, more preferably, 1:1.0-1.3.

More preferably, the mass percentage of the said GinsenosideRg5, the said GinsenosideRk1 and the said GinsenosideRg3 meets the following formula: $0.5 \leq (Rg5+Rk1)/Rg3 \leq 1.5$, more preferably, $0.5 \leq (Rg5+Rk1)/Rg3 \leq 1.0$.

More preferably, the said GinsenosideRg3 includes 20(R)-GinsenosideRg3 and 20(S)-GinsenosideRg3, of which the mass ratio is 1-1.5, more preferably, 1.1-1.2.

More preferably, the said *Panax* plant extract also contains GinsenosideRg2, GinsenosideRh1 and GinsenosideRh2; the mass percentage of the said GinsenosideRg3, the said GinsenosideRg5, the said GinsenosideRk1, the said GinsenosideRg2, the said GinsenosideRh1 and the said GinsenosideRh2 meets the following formula: $60\% \leq (Rg5+Rk1+Rg3)/(Rg5+Rk1+Rg3+Rg2+Rh1+Rh2) \leq 100\%$.

More preferably, the said GinsenosideRg2 includes 20(R)-GinsenosideRg2 and 20(S)-GinsenosideRg2, of which the mass ratio is 1.5-2.5, preferably, 1.8-2.0.

More preferably, the said *Panax* plant is selected from at least one of ginseng, red ginseng, Korean ginseng, pseudo-ginseng, *Panax japonicus* and American ginseng.

This application involves a pharmaceutical composition containing the *Panax* plant extract of this application and vectors acceptable to drug.

More preferably, the dosage form of the said pharmaceutical composition is selected from tablet, capsule, oral liquid, mouth agentia, granules, electuary, pill, pulvis, mastic, sublimed preparation, suspensoid, powder, solution, injection, suppository, spray, drops, patch. The said tablet is preferably orally disintegrating tablet.

The use of the *Panax* plant extract and the pharmaceutical composition of this application in preparing a drug for treating chronic heart failure, coronary stable angina, arrhythmia, diabetes and complications thereof, Meniere's disease, hyperlipemia, fatty liver, Alzheimer's disease, dymenorrhea, metabolic syndrome, gout, tumours or vascular leak syndrome.

Beneficial technical effects that the technical solution of this application can achieve are at least as below:

The *Panax* plant extract provided in this application contains a specific percentage of GinsenosideRg3, GinsenosideRg5 and GinsenosideRk1 with better biological activity.

DETAILED DESCRIPTION OF THE EMBODIMENTS

Below is the specific mode of carrying out this application, and the said embodiment is to further describe instead of restricting this application.

The embodiment of this application involves a *Panax* plant extract mainly composed of ginsenoside. When -Glc-Glc or -Glc-Ara (pyr) is deglycosylated at position 20, the original Panaxadiol Ginsenoside Rb1 and Rb2 can produce 20(S)-Rg3 and 20(R)-Rg3, and if dehydration occurs at the position 20 of 20(S)-Rg3 and 20(R)-Rg3, Rg5 and Rk1 can be produced. The *Panax* plant extract of the embodiment of this application mainly contains GinsenosideRg3, GinsenosideRk1, GinsenosideRg5, GinsenosideRg2, GinsenosideRh1 and GinsenosideRh2. For the *Panax* plant extract in the embodiment of this application, the *Panax* plant may be selected from ginseng, red ginseng, Korean ginseng, pseudo-ginseng, *Panax japonicus*, American ginseng and other *Panax* plants, and the usable part is the root, beard, stem, flower or leaf of the *Panax* plant, more preferably, the root and beard of the *Panax* plant.

GinsenosideRg5 and Rk1 are double-bond positional isomers between C-20 and C-22 formed by removing —OH on C-20 and —H on the ortho-position of Rg3. Their structural formulas are as follows:

In the embodiment of this application, the mass ratio of Rk1 and Rg5 is 1:1.0-1.5, more preferably 1:1.0-1.3, most preferably 1:1.15. By controlling the mass ratio of GinsenosideRk1 and GinsenosideRg5 in the *Panax* plant extract in this application, the physiological activity of the extract has been greatly improved.

As an improvement of the *Panax* plant extract in the embodiment of this application, the mass percentage of GinsenosideRg5, GinsenosideRk1 and GinsenosideRg3 meets the formula $0.5 \leq (Rg5+Rk1)/Rg3 \leq 1.5$, preferably, $0.5 \leq (Rg5+Rk1)/Rg3 \leq 1.0$, more preferably, $(Rg5+Rk1)/Rg3=0.85$, that is, by making the sum of the contents of GinsenosideRg5 and GinsenosideRk1 in the *Panax* plant extract of this application meet the said proportional relation with GinsenosideRg3, the sum of the contents of GinsenosideRg5 and GinsenosideRk1 has been fully increased, thus further improving their physiological activity.

GinsenosideRg3 includes 20(S)-GinsenosideRg3 and 20(R)-GinsenosideRg3, and is a C-20 enantiomer; their structural formulas are as follows:

As an improvement of the *Panax* plant extract in the embodiment of this application, the mass ratio of 20(R)-GinsenosideRg3 and 20(S)-GinsenosideRg3 meets the formula 1-1.5, preferably, 1.1-1.2, more preferably, 1.13.

GinsenosideRg2 includes 20(S)-GinsenosideRg2 and 20(R)-GinsenosideRg2, and is a C-20 enantiomer; their structural formulas are as follows:

As an improvement of the *Panax* plant extract in the embodiment of this application, the mass ratio of 20(R)-

GinsenosideRg2 and 20(S)-GinsenosideRg2 meets the formula 1.5-2.5, preferably, 1.8-2.0, more preferably, 1.92.

As an improvement of the *Panax* plant extract in the embodiment of this application, GinsenosideRg3, GinsenosideRg5, GinsenosideRk1, GinsenosideRg2, GinsenosideRh1 and GinsenosideRh2 meet the following formula:

60%≤(Rg5+Rk1+Rg3)/(Rg5+Rk1+Rg3+Rg2+Rh1+Rh2)≤100%;

more preferably,

80%≤(Rg5+Rk1+Rg3)/(Rg5+Rk1+Rg3+Rg2+Rh1+Rh2)≤100%.

That is, in this application, the sum of the mass of Rg5, Rk1, Rg3 is no less than 80% of that of Rg5, Rk1, Rg3, Rg2, Rh1, Rh2. That is, the embodiment of this application has fully increased the sum of the content of Rg5, Rk1, Rg3, thus further improving their physiological activity.

As an improvement of the *Panax* plant extract in the embodiment of this application, the sum of the mass of Rg5, Rk1, Rg3, Rg2, Rh1, Rh2 accounts for 50-80% of total mass of the *Panax* plant extract. The rest of ingredients are water, ash, pigment, carbohydrate, etc.

The *Panax* plant extract in the embodiment of this application can be prepared as follows:

(1) Extract with organic solvent and concentrate *Panax* plant materials;

(2) Mix the concentrated solution with 20-90% of acetic acid, treat the mixture on the condition of 40° C.-55° C. and 0.11 Mpa-0.15 MPa for 5-60 minutes, then 0° C.-5° C. and 0.13 MPa-0.18 MPa for 5-60 minutes, and then 60-110° C. for 0.5-5 hours, and get the hydrolysate; and (3) Gain the said *Panax* plant extract after resin absorption, removal of impurity, elution, concentration and drying.

As an improvement of the preparation method of the embodiment of this application, in step (1), the organic solvent can be alcohol organic solvent, preferably, ethyl alcohol;

As an improvement of the preparation method of the embodiment of this application, in step (2), for the concentration of volume percent of acetic acid, the lower limits are 20%, 22%, 25%, 27%, 30%, 32%, and the upper limits are 90%, 87%, 85%, 82%, 80%, 75%, 70%, 65%; its specific concentration can be a combination of random data of such upper and lower limits.

As an improvement of the preparation method of the embodiment of this application, in step (3), resin absorption is to absorb hydrolysate through macroporous resin.

As an improvement of the preparation method of the embodiment of this application, in step (3), the removal of impurity is to remove impurity through macroporous resin absorption column after elution with water, water containing soda and ethyl alcohol with concentration of less than 18%.

As an improvement of the preparation method of the embodiment of this application, in step (3), elution is to elute adsorption columns with ethyl alcohol with concentration of more than 32%.

As an improvement of the preparation method of the embodiment of this application, in step (3), concentration can be vacuum concentration.

As an improvement of the preparation method of the embodiment of this application, in step (3), drying can be selected from vacuum drying, baking, spray drying and freeze drying.

Analyze the *Panax* plant extract prepared in the embodiment of this application on the following chromatographic conditions:

Experimental materials: 20(S)-GinsenosideRg2, 20(R)-GinsenosideRg2, 20(R)-GinsenosideRh1, 20(S)-GinsenosideRh1, 20(S)-GinsenosideRg3, 20(R)-GinsenosideRg3, GinsenosideRk1, GinsenosideRg5 and GinsenosideRh2 reference substance with content of 98%; HPLC methyl alcohol; HPLC acetonitrile; purified water. Experimental apparatus: Shimadzu LC-2010A; ultrasonic apparatus; centrifugal machine; Vortex.

Preparation of reference solution: Precisely weigh and put in a 5 ml volumetric flask 10 mg of each reference substance, and dissolve and dilute it with methyl alcohol to a scale to make a stock solution with concentration of 2 mg/ml; precisely absorb and add to a 5 ml volumetric flask 500 μl of each stock solution, and dilute them with methyl alcohol to a scale to make a mixed standard solution with concentration of 0.2 mg/ml.

Preparation of test solution: Precisely weigh and put in a 5 ml volumetric flask about 10 mg of the *Panax* plant extract obtained from the Embodiment 1, dissolve and dilute it with methyl alcohol to a scale, weigh it, reweigh it after ultrasound treatment for 30 min and make up the lost weight with methyl alcohol, transfer it to a 10 ml centrifuge tube and centrifuge it at 4500 rpm for 10 min, filter the supernate through 0.45 μm filter membrane, and conduct injection analysis.

Chromatographic column: Agilent Zorbax SB-C18 (250× 4.6 mm, 5 μm); mobile phase: acetonitrile (A)-water (B); gradient: 1~10 min 18~25% A, 10~25 min 25~45% A, 25~45 min 45~65% A, 45~57 min 65~90% A, 57~58 min 90~18% A, 58~65 min 18% A; flow rate: 1.0 ml/min; column temperature: 40° C.; test wavelength: 203 nm; injection volume: 10 μl.

Figure 1:
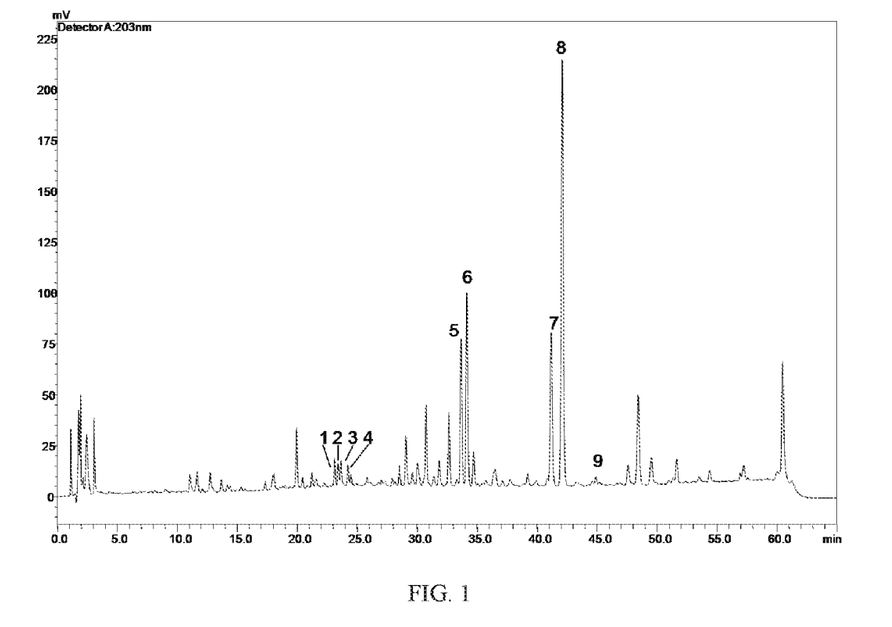
FIG. 1 shows the HPLC of the sample of total eriocitrin of ginseng.
Figure 2:
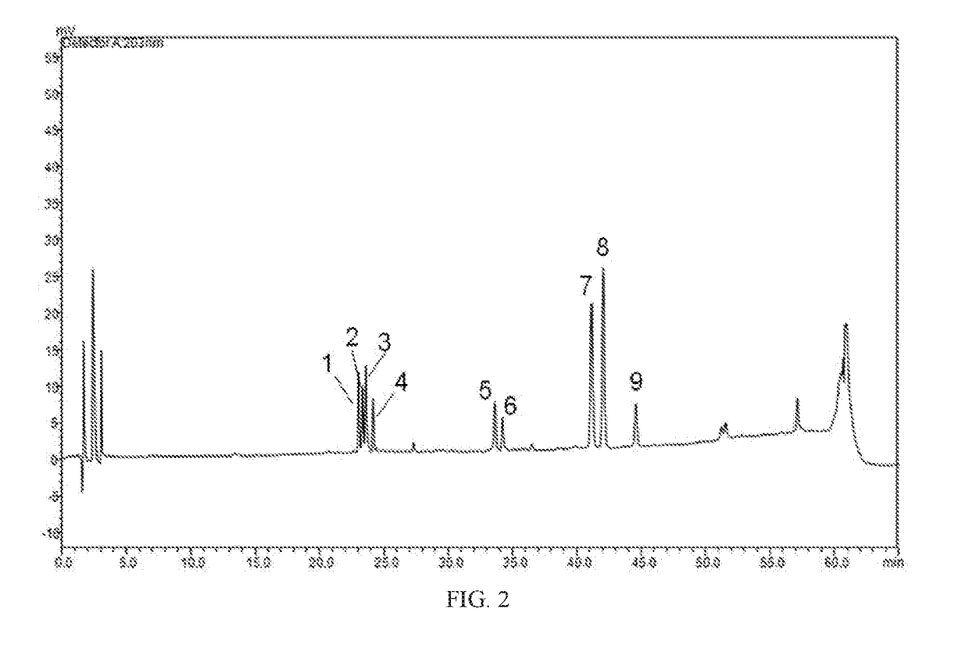
FIG. 2 shows the HPLC of the standard substance mixture of ginsenoside.

See FIG. 1 for the fingerprint gained by analysis. FIG. 2 shows the mixed standard solution of ginsenoside. See Table 1 for its content calculated with external standard method.

TABLE 1

Content of Ginsenoside in the Panax Plant Extract

| Fingerprint Map Peak No. | Name | Content (wt %) |
|---|---|---|
| 1 | 20(S)-GinsenosideRg2 | 1.16 |
| 2 | 20(R)-GinsenosideRg2 | 2.23 |
| 3 | 20(R)-GinsenosideRh1 | 0.90 |
| 4 | 20(S)-GinsenosideRh1 | 0.96 |
| 5 | 20(S)-GinsenosideRg3 | 7.45 |
| 6 | 20(R)-GinsenosideRg3 | 8.42 |
| 7 | GinsenosideRk1 | 6.32 |
| 8 | GinsenosideRg5 | 7.23 |
| 9 | GinsenosideRh2 | 0.96 |
| | Total Content | 35.63 |

As an improvement of the preparation method of the embodiment of this application, to further increase the yield rate, in step (1), the *Panax* plant material is first expanded in vacuum;

Preferably, steps of vacuum expansion treatment: Put the *Panax* plant material in the expansion tank, heat it for 5-40 mins until the temperature rises to 30-100° C., and the pressure to 0.1-0.9 MPa in the expansion tank, then quickly open the reducing valve connecting the expansion tank with the vacuum tank, which is vacuumized in advance, to instantly reduce the pressure to −0.04—0.08 MPa, and cool the tank for 5-40 mins. The yield rate can be increased by 5%-30%.

The embodiment of this application also involves a pharmaceutical composition of the *Panax* plant extract set out herein.

The pharmaceutical composition of the embodiment of this application can contain vectors acceptable to medicine as needed, in which the eriocitrin of ginseng is an active pharmaceutical ingredient accounting for 0.1-99.9% of the preparation in weight and the rest are vectors acceptable to medicine. The pharmaceutical composition of the embodiment of this application exists in the form of unit dose, which refers to the unit of preparation, such as each tablet, each capsule, each bottle for oral solution, each bag for granules and each injection.

The pharmaceutical composition of the embodiment of this application can be any medicinal dosage forms, including tablet (including orally disintegrating tablet, sugar-coated tablet, film-coated tablet and enteric coated tablet), capsule, hard capsule, soft capsule, oral liquid, mouth agentia, granules, electuary, pill, pulvis, mastic, sublimed preparation, suspensoid, powder, solution, injection, suppository, ointment, plaster, cream, spray, drops, patch.

For the pharmaceutical composition of the embodiment of this application, the preparations for its oral medication may contain common excipients, such as adhesive, filler, diluent, tableting aid, lubricant, disintegrating agent, colorant, condiment and wetting agent, and tablets can be coated if necessary.

Suitable fillers include cellulose, mannite, lactose and other similar fillers. Suitable disintegrating agents include starch, PVP and starch derivatives, such as sodium starch glycolate. Suitable lubricants include magnesium stearate. Suitable wetting agents acceptable to medicine include lauryl sodium sulfate.

Solid oral compositions can be prepared by mixing, filling, tabletting or with other common methods. Active materials can be mixed repeatedly to scatter in those compositions entirely using a great deal of fillers.

The form of oral liquid preparation can be aqueous or oily suspension, solution, emulsion, sirup, elixir or otherwise, or can be a dry product that can be compounded with water or other suitable vectors. This liquid preparation may contain conventional additives, including suspending agents (such as sorbitol, syrup, methylcellulose, gelatin, hydroxyethyl cellulose, carboxymethylcellulose, aluminium stearate gel or edible hydrogenated fat), emulgators (such as lecithin, sorbitan monooleate or Arabic gum), nonaqueous vectors (which can include edible oil and such as almond oil, fractionated coconut oil, oily ester such as glycerin rosin ester hydrogenated, propylene glycol or ethyl alcohol), preservatives (such as methyl paraben, propylparaben or sorbic acid), and if needed, can contain conventional flavouring agent or colorant.

For injection, the prepared liquid unit dosage form contains active materials and sterile vectors of the embodiment of this application. This compound can be suspended or dissolved according to vector and concentration. The solution is usually prepared by dissolving active materials in a vector, putting the filtered and sterilized compound in a suitable bottle or ampule and then sealing the bottle or ampule. Auxiliary materials such as a local anesthetics, preservative and buffer agent can be also dissolved in the vector. To make it more stable, the compound can be frozen after being put in the bottle and dehydrated in vacuum.

Suitable vectors acceptable to medicine can be selectively added when the pharmaceutical composition of the embodiment of this application is made into agentia. The vectors acceptable to the said medicine are selected from mannitol, sorbitol, sodium metabisulfite, sodium hydrogen sulfite, sodium thiosulfate, cysteine hydrochloride, thioglycolic acid, methionine, vitamin C, disodium EDTA, calcium disodium edetate, monovalent alkali carbonate, acetate, phosphate or its aqueous solution, hydrochloric acid, acetic acid, sulfuric acid, phosphoric acid, amino acid, sodium chloride, potassium chloride, sodium lactate, xylitol, maltose, glucose, fructose, dextran, glycine, starch, sucrose, Lactose, mannitol, silicon derivatives, cellulose and derivatives thereof, alginate, gelatin, polyvinylpyrrolidone, glycerin, earth temperature 80, agar, calcium carbonate, calcium hydrogencarbonate, surfactant, polyethylene glycol, cyclodextrin, β-cyclodextrin, phospholipid materials, kaolin, talc, calcium stearate, magnesium stearate, etc.

The usage and dosage of the pharmaceutical composition of the embodiment of this application in use depend on the conditions of patients. It can be taken three times a day, 1-20 doses a time, for example, 1-20 bags or pills or tablets, 1-1000 mg a dose.

In this application, the said pharmaceutical preparation can be prepared by ordinary technicians in this filed with methods generally known in this field.

The embodiment of this application also involves the use of the *Panax* plant extract in preparing a drug for treating chronic heart failure, coronary stable angina, arrhythmia, diabetes and complications thereof, Meniere, hyperlipemia, fatty liver, alzheimer, dymenorrhea, metabolic syndrome, gout, tumours or vascular leak syndrome.

Experimental Example 1: Experiment of Effectiveness on Alzheimer

1. Experimental materials: Accurately weigh 4 g of the *Panax* plant extract of the embodiment of this application, add pharmaceutical auxiliary material to the extract to make 100 tablets, each containing 40 mg of the *Panax* plant extract.

2. Experimental Method 99 patients (male 47, female 52) aged 55-85 (73.5±7.6) and with light and moderate alzheimer and MMSE score of 10-24 (16.3±2.6).

All AD patients use tablets three times a day, one tablet a time for 12 consecutive weeks. Before and once 4 weeks after using the drug, the patients take a medical as follows:

(1) Screen AD with MMSE. Test the patients' cognitive function (orientation, memory, calculation ability, language competence, ability for using view space segment, etc);

(2) Test the dementia degree of the patients with CDR; and (3) Test the patients' daily self-help ability with ADL. The statistical software SPSS is used for test results, and before and after the treatment, t test is used for both the GinsenosideRg3 naristillae group and the placebo control group.

See Table 2 for the scoring results of MMSE, CDR and ADL of AD patients.

TABLE 2

Scoring Results of MMSE, CDR and ADL of AD Patients before and after Treatment with the Panax Plant Extract Tablets (x ± s, score)

| Scale | Before Treatment | Treatment for 4 Weeks | Treatment for 12 Weeks |
| --- | --- | --- | --- |
| MMSE | 16.4 ± 2.8 | 19.2 ± 1.9* | 20.7 ± 1.6** |
| CDR | 2.2 ± 0.4 | 1.7 ± 0.2 | 1.4 ± 0.2* |
| ADL | 49.8 ± 8.3 | 47.1 ± 7.8 | 41.5 ± 7.2* |

Note:
Comparison of self-control group before and after treatment, *P < 0.05, **P < 0.01.

Compared with those before treatment, cognitive function (scored with MMSE) has been significantly improved after treatment for 12 weeks, and the MMSE score has increased by 4.3 points (P<0.01) and been significantly improved after using the drug for 4 weeks (P<0.05). Compared with those before treatment, dementia degree (scored with CDR) has been significantly reduced after treatment for 12 weeks, and the CDR score has decreased by 0.8 points (P<0.05). Compared with those before treatment, daily self-help ability (scored with ADL) has been significantly reduced after treatment, and the ADL score has decreased by 8.3 points (P<0.01).

In conclusion, the *Panax* plant extract of this application is safe and effective for improving AD patients' light and moderate cognition impairment, decline in self-help ability and dementia degree.

Experimental Example 2: Blood Glucose Reduction Contrast Experiment

1. Experimental Materials
1.1 Drug and Reagent
Investigational Drug: The *Panax* plant extract obtained from the embodiment of this application.

With components shown in Table 3, the contrast preparation 1 is made from standard substance.

TABLE 3

| Component | Name | Content (wt %) |
|---|---|---|
| 1 | 20(S)-GinsenosideRg2 | 1 |
| 2 | 20(R)-GinsenosideRg2 | 2 |
| 3 | 20(R)-GinsenosideRh1 | 1 |
| 4 | 20(S)-GinsenosideRh1 | 1 |
| 5 | 20(S)-GinsenosideRg3 | 8 |
| 6 | 20(R)-GinsenosideRg3 | 8 |
| 7 | GinsenosideRk1 | 2 |
| 8 | GinsenosideRg5 | 12 |
| 9 | GinsenosideRh2 | 1 |
| 10 | distilled water | 64 |

The investigational drug and the contrast preparation 1 were respectively made into solution with 0.5% carboxymethylcellulose for intragastric administration.
Streptozotocin: (sigma).
1.2 Animal
Wistar rats weighing 180±20 g and purchased from Shandong University Laboratory Animal Center.
2. Experimental Method
2.1 Hyperglycemia Modeling
Select 20 qualified rats and divide them into 4 groups: normal control group, model animal group, group for this application and control group. Rats in the model animal group, group for this application and control group were tail-intravenously injected with streptozotocin according to 65 mg/kg 3 days prior to the start of the experiment, and according to the blood glucose testing, the modeling was successful.
2.2 Drug Administration
Animals in the normal control group were orally given equivalent purified water;
Successfully molded animals in the model animal group were orally given equivalent purified water;
Successfully molded animals in group for this application were given the *Panax* plant extract of the embodiment of this application for 14 consecutive days; and
Successfully molded animals in group for this application were given the contrast preparation 1 according to 200 mg/kg/d for 14 consecutive days.
During the experiment, fodders and water were freely taken in. Blood glucose of animals in each group was determined before and on the 7$^{th}$ and 14$^{th}$ days after drug administration, respectively. In each test, at 10:00 am, blood was collected from caudal vein of rats without anesthesia to determine the blood sugar concentration in their blood.
3. Experimental Results
Processed with SPSS11.0, all data first took normality test and homogeneity test of variance. The determination results of the blood sugar concentration in the blood of each group of rats were compared using one-way analysis of variance, and SNK-q test at the level of α=0.05 was used for pairwise comparison among groups. See Table 4 for the determination results.

TABLE 4

Effect of the Panax Plant Extract on the Blood Sugar Concentration of Rats (mg/dL) (x ± s, n = 5)

| Group | Before Drug Administration | 7th Day after Drug Administration | 14th Day after Drug Administration |
|---|---|---|---|
| Normal Control Group | 67.8 ± 4.2 | 75.3 ± 3.5 | 70.2 ± 5.3 |
| Model Animal Group | 281.4 ± 33.2 | 327.3 ± 23.7 | 410.4 ± 36.3 |
| Control Group | 280.3 ± 31.4 | 216.3 ± 19.2# | 311.2 ± 27.2# |
| Group for This Application | 282.6 ± 30.7 | 157.2 ± 24.3#* | 248.6 ± 25.1#* |

Note:
Compared with the model animal group: #P < 0.05; compared with the control group: *P < 0.05.

Experimental Example 3: Blood Fat Reduction Contrast Experiment

1. Experimental Materials
1.1 Drug and Reagent
Investigational Drug: The *Panax* plant extract obtained from the embodiment of this application.
The composition of the contrast preparation 1 was the same as that of the Experimental Example 1.
The investigational drug and the contrast preparation 1 were respectively made into solution with 0.5% carboxymethylcellulose for intragastric administration.
TC and TG Kits.
1.2 Animal
Wistar rats weighing 180±20 g and purchased from Shandong University Laboratory Animal Center.
1.3 Apparatus
UV85 ultraviolet spectrophotometer (Techcomp Shanghai), Hitachi 7170A fully automatic biochemical analyser.
2. Experimental Method
2.1 Hyperlipidemia Modeling
Divide 20 Wistar rats into 4 groups: normal control group, model animal group, group for this application and control group. Rats in the model animal group, group for this application and control group were fed with high-fat diet, and in the normal control group were fed with ordinary fodder. They were weighed once a week; in the 4$^{th}$, 6$^{th}$ and 8$^{th}$ weeks, 1-2 animals in the fatty liver model animal group were randomly selected, and 1 ml of blood was tail-intravenously collected from it or them to observe the dynamic change of blood fat; at the end of the 8$^{th}$ week, for the fatty liver model animal group, the blood fat significantly rose with moderate and severe fatty changes in liver, meaning successful modeling.
High-fat Diet Formula: standard diet+1% cholesterol+ 14% lard oil.

2.2 Method of Drug Administration

Normal control group and model animal group: Intragastric administration with distilled water;

Control group was given the contrast preparation 1 according to 200 m g/kg/d for 14 consecutive days;

This application group was given the *Panax* plant extract of the embodiment of this application according to 200 m g/kg/d for 14 consecutive days.

Standard diet was given in drug administration.

2.3 Specimen Preparation

At the end of the $8^{th}$ week, decapitate it for blood 12 hours after its last feed. Separate the serum through low-temperature centrifugation, seal it tightly and place it under −20° C. cold storage for examination.

2.4 Index Detection

Place the serum under cold storage in a constant temperature water box under 37° C. to unfreeze it, take proper amount of serum and determine the content of TC (total cholesterol) and TG (triglyceride) based on the requirements of reagent kits.

4. Experimental Results

Determine content of TC and TG of the rat's liver based on the requirements of reagent kits, the results are shown in Table 5.

TABLE 5

Effects of Panax plants Extract on the TC and TG of the Experimental Rat's Liver (X ± S, n = 6)

| Group | TC (mmol/L) | TG (mmol/L) |
|---|---|---|
| Normal Control Group | 0.76 ± 0.22 | 1.33 ± 0.26 |
| Model Group | 1.26 ± 0.23 | 2.15 ± 0.74 |
| Control Group | 0.98 ± 0.18# | 1.86 ± 0.17# |
| Group for This Application | 0.81 ± 0.07*# | 1.36 ± 0.13*# |

Note:
P < 0.05 compared with the model animal group, and *P < 0.05 compared with the control group.

Embodiment 4: Contrast Experiment for Dysmenorrhea

2. Experimental Materials 1.1 Medicine and Reagent

Investigational product: *Panax* plant extract in the embodiment of this application.

The composition of contrast preparation 2 is shown in Table 6:

TABLE 6

| Composition | Name | Content (wt %) |
|---|---|---|
| 1 | 20(S)-ginsenoside Rg2 | 1 |
| 2 | 20(R)-ginsenoside Rg2 | 2 |
| 3 | 20(R)-ginsenoside Rh1 | 1 |
| 4 | 20(S)-ginsenoside Rh1 | 1 |
| 5 | 20(S)-ginsenoside Rg3 | 9 |
| 6 | 20(R)-ginsenoside Rg3 | 9 |
| 7 | Ginsenoside Rk1 | 2 |
| 8 | Ginsenoside Rg5 | 1 |
| 9 | Ginsenoside Rh2 | 10 |
| 10 | distilled water | 64 |

The investigational drug, the contrast preparation 1 and the contrast preparation 2 were respectively made into solution with 0.5% carboxymethylcellulose for intragastric administration.

Diethylstilbestrol Injection, Shanghai General Pharmaceutical Co., Ltd.

Oxytocin Injection, Nanjing Biochemistry Pharmaceutical Factory 1.2 Animal

Female SD rats, weighing 160-180 g and purchased from Shandong University Laboratory Animal Center.

1.3 Apparatus

PB303-N electronic scales, from METTLER TOLEDO INSTRUMENTS (SHANGHAI) CO., LTD.

PowerLab/8s, and its bundled software are provided by AD Apparatus in Australia.

2. Methods and Results 2.1 Animal Model Preparation

40 Female SD rats, in 4 random groups, which means blank control group, model animal group, control group, and the group for this application. Except for the blank control group, rats in all groups shall be subcutaneously injected with diethylstilbestrol in 10 consecutive days, with one injection for each day, and 0.8 mg shall be injected to every rat on the $1^{st}$ day and the $10^{th}$ day, while 0.2 mg shall be injected from the 2' day to the $9^{th}$ day in the same manner.

2.2 Method of Administering Medicines

The same amount of distilled water shall be administered to the blank control group and the model animal group.

Control group: from the $5^{th}$ day on, contrast preparation 2 shall be administered based on the rule of 200 mg/kg/d.

The group for this application: from the $5^{th}$ day on, *Panax* plant extract shall be administered to the embodiment of this application.

2 units of oxytocin shall be injected to abdominal cavities of every rat 1 hour after the last administration of diethylstilbestrol on the $9^{th}$ day. Then observe the pain reaction of rats in all groups within 30 minutes, writhing response shall be deemed as a dysmenorrhea index of uterine contraction (UC) when the abdomen of a rat constricts inward, with stretching body and hind limbs and intorsion of haunch and one side of the body. Observe and record the quantity of writhing rats suffered from dysmenorrhea and average writhing times of rats and calculate the dysmenorrhea rate, see the results in Table 7.

TABLE 7

Effects of Panax Plants Extract on Rat Dysmenorrhea Model

| Group | Number of Animals (n) | Dosage of Administration (g/kg) | Writhing Times within 30 mins (n) | Dysmenorrhea Rate (%) |
|---|---|---|---|---|
| Blank Control Group | 10 | Same amount of distilled water | 0 | — |
| Model Group | 10 | Same amount of distilled water | 9 | 90 |
| Control Group | 10 | 2.0 | 5# | 50 |
| Group for This Application | 10 | 0.5 | 1*# | 10 |

Note:
P < 0.05 when compared with the model animal group, and *P < 0.05 when compared with the control group.

Embodiment 5: Contrast Experiments for Thrombus

2. Experimental Material

40 SD rats weighs 250-300 g with the same quantity for each sex, purchased from Shandong University Laboratory Animal Center.

Investigational product: *Panax* plant extract in the embodiment of this application.

For contrast preparation 1, the composition is shown in Table 3.

For contrast preparation 2, the composition is shown in Table 6.

The investigational drug, the contrast preparation 1 and the contrast preparation 2 were respectively made into solution with 0.5% carboxymethylcellulose for intragastric administration.

2. Experimental Method

Separate the rats into 4 random groups (model animal group, control group 1, control group 2 and experimental group), the specific drug administration is:

Control group 1: contrast preparation 1 shall be administered based on the rule of 200 mg/kg/d.

Control group 2: contrast preparation 2 shall be administered based on the rule of 200 mg/kg/d.

Experimental group: *Panax* plant extract in the embodiment of this application shall be administered based on the rule of 200 mg/kg/d.

Model group: pure water;

Feed above-mentioned medicine through gavage for 7 days.

2. Determination of Inhibition Rate of Thrombosis

On the $7^{th}$ day of drug administration, each rat shall be anaesthetized with pentobarbital sodium 30 minutes after administration. Separate left external jugular vein from right carotid artery, fetch three sections of cannula formed by polyethylene tubes, a 5 cm weighed No. 4 surgical suture shall be placed in the middle section, fill the polyethylene tubes with heparin physiological saline (50 U/ml), when one end of the tube is inserted into external jugular vein, clamp that end of the tube and insert the end fixed by silk thread into right carotid artery, open the bloodstream after the operation is completed, and interrupt the process 15 minutes later, then weigh the promptly fetched silk thread, deduct silk thread weight from gross weight and obtain wet weight of thrombus.

Inhibition Ratio=(wet weight of thrombus in model animal group-wet weight of thrombus in experimental group)/wet weight of thrombus in model animal group.

Conduct statistical treatment to the average values of weight of thrombus in all groups, and determine the significant effects of medicine and effect intensity through t-test and inhibition ratio respectively.

3. Experimental Results

As shown in Table 8:

TABLE 8

Effects of Panax Plants Extract on Rat Thrombus Model

| Group | Dosage (mg/kg) | Number of Animals (n) | Wet Weight of Thrombus (g) | Inhibition Ratio |
|---|---|---|---|---|
| Model Group | — | 10 | 0.0277 ± 0.007 | — |
| Control Group 1 | 200 | 10 | 0.0233 ± 0.006 | 15.9% |
| Control Group 2 | 200 | 10 | 0.0243 ± 0.007 | 12.3% |
| Group for This Application | 200 | 10 | 0.0209 ± 0.005 | 24.5%#* |

Note:
P < 0.05 when compared with control group 1, and *P < 0.05 when comopared with control group 2.

Embodiment 6: Tumour Contrast Experiment

4. Experimental Materials

Used tumor cell strains: human non-small cell lung cancer A549 cells, MGC80-3 human gastric cancer cells, three kinds of human tumor cell lines of MCF-7 human breast cancer cells (RPMI 1640, DMEM and MEM nutrient solutions are respectively used for cell culture.)

Investigational product: *Panax* plant extract in the embodiment of this application.

Comparative preparation 1, The composition is shown in Table 3.

Comparative preparation 1, The composition is shown in Table 6.

In the embodiment of this application, *Panax* plant extract is dissolved in dimethyl sulfoxide (DMSO) solution, and shall be diluted to the required concentration respectively: 1, 25, 50, 200 ug/L with RPM 1-1640, DMEM and MEM nutrient solutions for cell culture.

Comparative preparation 1 is dissolved in dimethyl sulfoxide (DMSO) solution, and shall be diluted to the required concentration respectively: 1, 25, 50, 200 ug/L with RPM 1-1640, DMEM and MEM nutrient solutions for cell culture.

Comparative preparation 2 is dissolved in dimethyl sulfoxide (DMSO) solution, and shall be diluted to the required concentration respectively: 1, 25, 50, 200 ug/L with RPM 1-1640, DMEM and MEM nutrient solutions for cell culture.

5. Method

Collect cells of logarithmic phase and add 0.25% trypsin for digestion, centrifugate it for 10 minutes under 600 r/min, adjust cell concentration to $6*10^4$/mL and inoculate them onto 96 well cell culture plate (the wells on the edge shall be filled with sterile PBS), with 90 μL for every well. After 24 hours of culturing, the nutrient solution contains different concentration of experimental samples shall be added respectively, and the final DMSO concentration shall be lower than 1%, there are 3 parallel wells in every group. Culture them in the incubator under 37° C. with 5% $CO_2$ concentration for 48 hours. 20 μL of MTT solution (5 mg/mL, dissolved in PBS) shall be added into every well, culture them for another 4 hours and end it. Absorb and discard the supernate carefully then add 150 μL of DMSO and shake them for 10 minutes to fully dissolve the crystal substance. Use the Elisa Reader to measure the light absorption value (A) of every well at 570 nm location and calculate cell survival rate.

cell survival rate %=A value of added samples/A value of cells in control group*100%

6. Results

The experimental results indicates that *Panax* plant extract in the embodiment of this application has relatively strong cell killing effects on all three kinds of human tumor cell lines, and the effects are obviously stronger compared with the ones in comparative examples. See results in Table 9-11.

TABLE 9

Effects of Panax Plants Extract on Human
Non-small Cell Lung Cancer A549 cells

| Medicine | Survival Rate of Cancer Cells (%) | | |
|---|---|---|---|
| Concentration (μg/L) | This Application | Comparative Example 1 | Comparative Example 2 |
| 0 | 100 | 100 | 100 |
| 1 | 85.4 ± 1.1 | 93.2 ± 1.2 | 91.1 ± 1.3 |
| 25 | 72.6 ± 1.2 | 83.3 ± 1.3 | 81.2 ± 1.2 |
| 50 | 63.4 ± 1.3 | 74.5 ± 1.2 | 66.4 ± 1.3 |
| 100 | 50.1 ± 1.2 | 65.3 ± 1.1 | 62.5 ± 1.2 |
| 200 | 47.8 ± 1.3 | 59.4 ± 1.0 | 57.6 ± 1.1 |

TABLE 10

Effects of Panax plants Extract on MGC80-3
Human Gastric Cancer Cells

| Medicine | Survival Rate of Cancer Cells (%) | | |
|---|---|---|---|
| Concentration (μg/L) | This Application | Comparative Example 1 | Comparative Example 2 |
| 0 | 100 | 100 | 100 |
| 1 | 85.4 ± 1.1 | 89.2 ± 1.2 | 90.3 ± 1.1 |
| 25 | 67.6 ± 1.2 | 71.3 ± 1.3 | 70.4 ± 1.2 |
| 50 | 57.4 ± 1.3 | 61.5 ± 1.2 | 59.2 ± 1.2 |
| 100 | 41.1 ± 1.2 | 51.3 ± 1.1 | 51.8 ± 1.2 |
| 200 | 33.8 ± 1.3 | 43.4 ± 1.0 | 42.4 ± 1.3 |

TABLE 11

Effects of Panax Plants Extract on MCF-7
Human Breast Cancer Cells

| Medicine | Survival Rate of Cancer Cells (%) | | |
|---|---|---|---|
| Concentration (μg/L) | This Application | Comparative Example 1 | Comparative Example 2 |
| 0 | 100 | 100 | 100 |
| 1 | 85.4 ± 1.1 | 90.2 ± 1.2 | 89.2 ± 1.1 |
| 25 | 68.6 ± 1.2 | 70.3 ± 1.3 | 71.3 ± 1.2 |
| 50 | 46.4 ± 1.3 | 49.5 ± 1.2 | 60.5 ± 1.2 |
| 100 | 38.3 ± 1.2 | 43.3 ± 1.1 | 52.3 ± 1.3 |
| 200 | 31.8 ± 1.3 | 38.4 ± 1.0 | 41.4 ± 1.1 |

Embodiment 1

Preparation Method of *Panax* Plant Extract Include the Following Steps:

(6) Ginseng slices shall undergo reflux extraction with 60% ethyl alcohol for three times, with quadruple volume of solution for 3 hours every time, then get the extracting solutions and combine them then depressurize them for concentration.

(7) Mix the concentrated solution with 60% acetic acid in the same volume, dip it for 20 minutes under 40° C., 0.11 MPa, then dip it for 20 minutes under 5° C., 0.15 MPa, raise the temperature to 90° C. and heat it for 2 hours to get hydrolysate.

(8) Pass the hydrolysate through D101 macroporous resin column.

(9) The absorption column penetrates the macroporous absorption resin shall go through water elution, and shall be eluted with 0.5% sodium hydroxide, then go through water elution again until it is neutral and remove the impurities after being eluted with 15% ethyl alcohol.

(10) Elute it with 50% ethyl alcohol, collect the eluent fluid, depressurize and concentrate it until it concretes, vacuum-dry it under 70° C. and get the *Panax* plant extract for this application.

When the prepared *Panax* plant extract is analyzed through the above-mentioned HPLC, the acquired atlas is similar to that of FIG. 1. Other Ginseng plants are also used: red ginseng, Korean ginseng, notoginseng, *Panax japonicus*, American ginseng, etc. They are prepared under the same specific conditions as employed in this embodiment, so the acquired HPLC of *Panax* plant extract is similar to that of FIG. 1.

Embodiment 2

Preparation Method of *Panax* Plant Extract Include the Following Steps:

(1) Vacuum puffing treatment: place the notoginseng in a puffing tank, heat it and keep the temperature at 80° C., raise the pressure to 0.5 Mpa and maintain the conditions for 20 minutes. The air in vacuum tank shall be removed in advance, open the relief valve which connects the puffing tank with the vacuum tank, depressurize it to −0.04 MPa. Cool it and maintain the conditions for 20 minutes.

(2) Notoginseng slices shall undergo reflux extraction with 50% ethyl alcohol for three times, with double volume of solution for 2 hours every time, then get the extracting solutions.

(3) Mix the extracting solution with 80% acetic acid in the same volume, dip it for 15 minutes under 55° C., 0.15 MPa, then dip it for 25 minutes under 0° C., 0.18 MPa.

(3) Pass the hydrolysate through D101 macroporous resin column.

(4) The absorption column penetrates the macroporous absorption resin shall go through water elution, and shall be eluted with 0.5% sodium hydroxide, then go through water elution again until it is neutral and remove the impurities after being eluted with 12% ethyl alcohol.

(5) Elute it with 55% ethyl alcohol, collect the eluent fluid, depressurize and concentrate it until it concretes, vacuum-dry it under 70° C. and get the *Panax* plant extract for this application.

When the prepared *Panax* plant extract is analyzed through the above-mentioned HPLC, the acquired atlas is similar to that of FIG. 1. Other Ginseng plants are also used: red ginseng, Korean ginseng, notoginseng, *Panax japonicus*, American ginseng, etc. They are prepared under the same specific conditions as employed in this embodiment, so the acquired HPLC of *Panax* plant extract is similar to that of FIG. 1.

What is claimed is:

1. A *Panax* plant extract, wherein the *Panax* plant extract comprises GinsenosideRg3, GinsenosideRk1 and GinsenosideRg5, wherein a mass ratio of the GinsenosideRk1 to the GinsenosideRg5 is 1:(1.0-1.3);

wherein the GinsenosideRg3 comprises 20(R)-GinsenosideRg3 and 20(S)-GinsenosideRg3 with a mass ratio of (1-1.5):1;

the *Panax* plant extract further comprises GinsenosideRg2, GinsenosideRh1, GinsenosideRh2, and 80%≤(Rg5+Rk1+Rg3)/(Rg5+Rk1+Rg3+Rg2+Rh1+Rh2) <100%, and 0.5≤(Rg5+Rk1)/Rg3 ≤1.0, wherein Rg3 is a mass percentage of the GinsenosideRg3, Rg5 is a mass percentage of the GinsenosideRg5, Rk1 is a mass percentage of the GinsenosideRk1, Rg2 is a mass percentage of the GinsenosideRg2, Rh1 is a mass percentage of the GinsenosideRh1 and Rh2 is a mass percentage of the GinsenosideRh2;

wherein a sum of a mass of Rg5, Rk1, Rg3, Rg2, Rh1, Rh2 accounts for 50-80% of total mass of the *Panax* plant extract;

wherein the plant extract is prepared as follows:
1) extracting with an organic solvent and concentrating *Panax* plant materials to obtain a concentrated solution;
2) mixing the concentrated solution with 20-90% of acetic acid to obtain a mixture, treating the mixture on conditions of 40° C.-55° C. and 0.11 Mpa-0.15 Mpa for 5-60 minutes, and then 0° C.-5° C. and 0.13 Mpa-0.18 Mpa for 5-60 minutes, and then 60-110° C. for 0.5-5 hours, and obtaining a hydrolysate; and
3) performing a resin absorption, a removal of impurity, an elution, a concentration and drying to obtain the *Panax* plant extract.

2. The *Panax* plant extract of claim 1, wherein the mass ratio of the 20(R)-GinsenosideRg3 and the 20(S)-GinsenosideRg3 is (1.1-1.2):1.

3. The *Panax* plant extract of claim 1, wherein the GinsenosideRg2 comprises 20(R)-GinsenosideRg2 and 20(S)-GinsenosideRg2 with a mass ratio of (1.5-2.5):1.

4. The *Panax* plant extract of claim 1, wherein the *Panax* plant extract comes from a *Panax* plant, and the *Panax* plant is at least one selected from the group consisting of ginseng, red ginseng, Korean ginseng, pseudo-ginseng, *Panax japonicus* and American ginseng.

5. A pharmaceutical composition, comprising the *Panax* plant extract of claim 1 and vectors acceptable to drug.

6. The pharmaceutical composition of claim 5, wherein a dosage form of the pharmaceutical composition is one selected from the group consisting of tablet, capsule, oral liquid, mouth agentia, granules, electuary, pill, pulvis, mastic, sublimed preparation, suspensoid, powder, solution, injection, suppository, spray, drops, and patch, and the tablet is an orally disintegrating tablet.

7. The pharmaceutical composition of claim 5, wherein the mass ratio of the 20(R)-GinsenosideRg3 and the 20(S)-GinsenosideRg3 is (1.1-1.2):1.

8. The pharmaceutical composition of claim 7, wherein the GinsenosideRg2 comprises 20(R)-GinsenosideRg2 and 20(S)-GinsenosideRg2 with a mass ratio of (1.5-2.5):1.

9. The pharmaceutical composition of claim 5, wherein the *Panax* plant extract comes from a *Panax* plant, and the *Panax* plant is at least one selected from the group consisting of ginseng, red ginseng, Korean ginseng, pseudo-ginseng, *Panax japonicus* and American ginseng.

* * * * *